United States Patent [19]

Merce Vives

[11] Patent Number: 5,800,138
[45] Date of Patent: Sep. 1, 1998

[54] EXTRACORPOREAL BLOOD PUMP FOR CARDIAC SURGERY

[76] Inventor: Salvador Merce Vives, Ruzafa, 23, 46004 Valencia, Spain

[21] Appl. No.: 692,866

[22] Filed: Jul. 30, 1996

[51] Int. Cl.$^6$ .................. F04B 9/14; F04B 17/00
[52] U.S. Cl. .......... 417/374; 417/420; 417/410.3; 418/36; 418/37; 418/69; 604/4
[58] Field of Search .................. 417/374, 411, 417/410.3, 420; 418/35, 36, 37, 69; 604/4, 5, 131, 151

[56] References Cited

U.S. PATENT DOCUMENTS

| | | | |
|---|---|---|---|
| 2,270,976 | 1/1942 | Sobek | 418/37 |
| 2,566,743 | 9/1951 | Okulitch et al. | 417/420 |
| 3,420,184 | 1/1969 | Engelesberg et al. | 417/420 |

FOREIGN PATENT DOCUMENTS

| | | | |
|---|---|---|---|
| 101592 | 6/1984 | Japan | 418/36 |

*Primary Examiner*—Charles G. Freay
*Attorney, Agent, or Firm*—Schweitzer Cornman Gross & Bondell LLP

[57] ABSTRACT

An extracorporeal blood pump for cardiac surgery is disclosed having a housing with a cylindrical cavity, radially-spaced input and output ports and a pair of radial blades within the cavity. The blades are supported on independent, concentric axles such that one blade can remain between the ports while the other blade rotates to create independent input and output chambers. Magnetic elements attached to the axles are in magnetic coupling relation to corresponding magnetic elements of two independent motors. The blades and magnetic elements corrected thereto are covered in plastic and are hermetically sealed within the housing. A programmable logic controller controls the motion and the blades to simulate the pulsatile pumping of a human heart. The axles of the blades can extend out one side of the housing for engagement by a manual activation device operable to continuously alternately rotate one of the axles one half rotation while holding the other axle motionless.

11 Claims, 5 Drawing Sheets

EXTRACORPOREAL BLOOD PUMP FOR CARDIAC SURGERY

THE INVENTION's PURPOSE

This invention refers to a blood pump system, specially conceived to maintain a patient's circulation while undergoing cardiac surgery, but with a special feature, that system allows one to obtain an adjustable pulsatile flow, to suit the particular characteristics of each patient or individual, specifically his own pulse or the one the physician determines.

THE INVENTION's BACKGROUND

It is well know, that intracardiac surgery (open heart surgery), due to technical causes, requires an immobile and bloodless operatory field during the operation: and bloodless operatory field during the operation; and to do this the heart needs to stop working and be substituted temporarily by means of an external pumping system, this way maintaining blood perfusion to the brain and other vital organs of the body.

Obviously, in this pump system, a determining part of it corresponds to the pump, as this is the piece that gives it meaning.

To date, there are different types of blood pumps for extracorporeal circulation, one which should be pointed out is the centrifugal pump, which creates a continuous blood flow, with a determined pressure, through turbines, whose use is not advisable since this continuous blood flow differs considerably from the pulsatile and natural flow produced by the human heart.

There are other types of pumps, based on alternating pistons, rollers and likewise, which in cooperation with valves produce only an intermittent flow, but when put to use only provide for a "square" wave flow, significantly far from a sinewave and even more so from the heart's pulsatile wave.

The larger the disparity between a natural blood flow and the flow produced by the pumping system, the greater will be the patient's physiological deterioration; the increase of vascular resistance, aggregation of red corpuscles, lymphatic stagnancy and edema, tissular hypoxia and metabolic acidosis, etc.

Therefore, it seems logical and desirable to obtain an extracorporeal blood flow as similar as possible to a natural pulsatile flow.

SUMMARY OF THE INVENTION

This invention proposes an extracorporeal blood pumping system that allows for reaching the objective specified in the previous section, with a structurally simple solution and an absolutely reliable performance, whose low cost allows for single use, that is to say that the pump can be disposed of after using it for the first and only time in one patient.

For this and to be more specific, the envisaged system has a pump with a fixed body or housing, basically cylindric, provided with input and output ports, radially positioned and situated relatively near each other. Operating inside the housing are a pair of blades associated to a driving axle, each one of these blades setting a radial lock inside the housing and with the particularity that these blades do not move simultaneously, but instead when one is in movement the other is still, and vice versa. To be more specific, the locking position of these blades is set between the said ports, in such a way that as one blade moves with respect to the other, from this point of limited lateral contact, the output chamber progressively reduces it volumetry, while at the same time the input chamber increases it volumetry, with the consequent and parallel operation of intake and impulsion blood, which can be conveniently controlled by means of the driving control of the axle of each of these blades.

To be more specific, the blades and the housing are made of biocompatible material. Each of the blades is mounted on an independent axle, which axles have integral magnetic parts. Each of the axles is activated by an independent servomotor with corresponding magnetic elements. Thus, the axles and blades can be driven without direct physical connections thereto.

These servomotors, which control the movement of the blades and consequently the pump's real flow, are governed by a Programmable Logic Control (PLC) which can be controlled through a digitalized screen, or through a conventional PC, whose components can be conveniently situated in a cabinet.

According to another one of the invention's characteristics, there is sufficient clearance between the housing and the blades to avoid the shearing effect on blood components such as red cells, platelets, etc..

Finally and per another one of the invention's characteristics, the pump in itself has been provided with a manual activated mechanical system, which permits it to keep operating in the event of a failure of power.

A mechanical transmission system has been developed for other applications which allows for the alternating movement of the blades.

BRIEF DESCRIPTION OF THE DRAWINGS

To complete the description provided herewith and in order to help improve the understanding of this invention's characteristics, enclosed with and forming an integral part of this descriptive description, is a set of drawings, which with an illustrative but not limitative character, the following is represented.

DETAILED DESCRIPTION OF THE INVENTION

Figure 1:
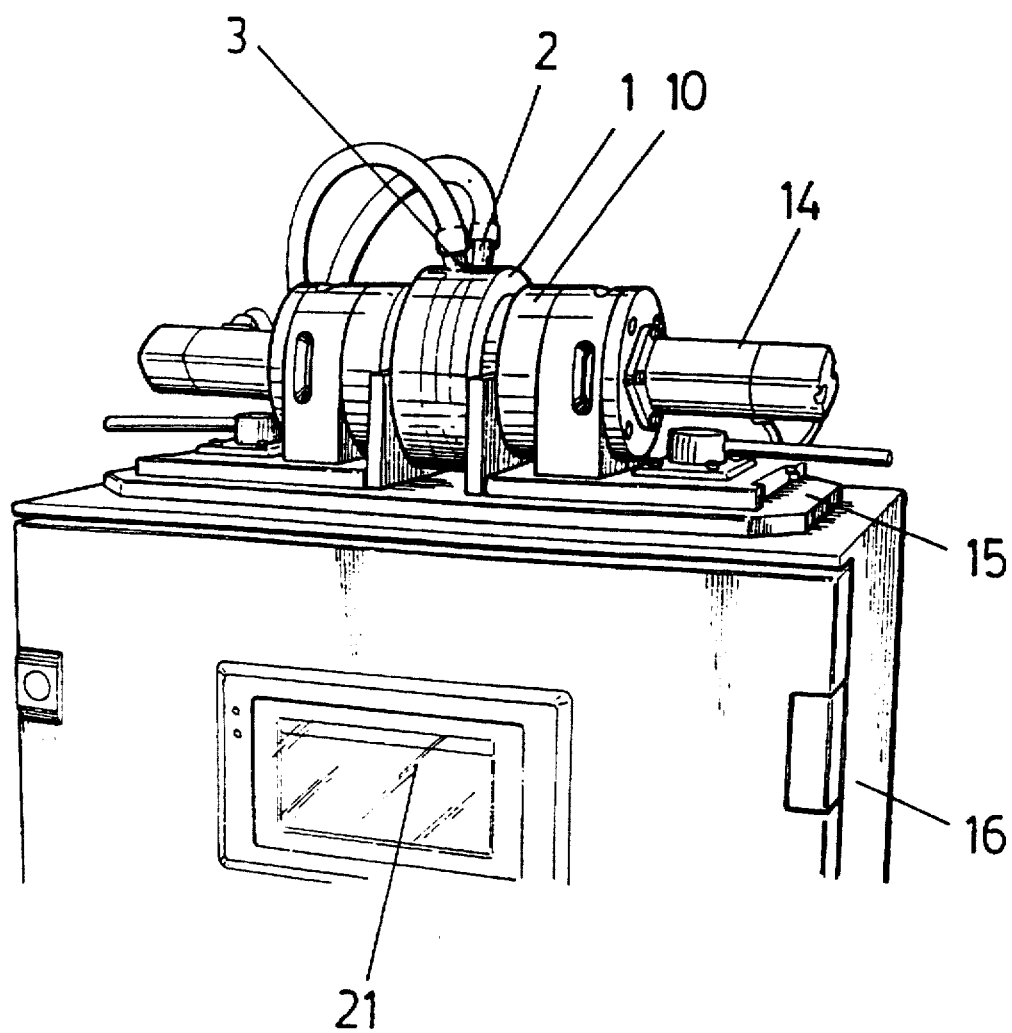
FIG. 1 is a perspective view of a pump made in accordance with the invention from the front.
Figure 2:
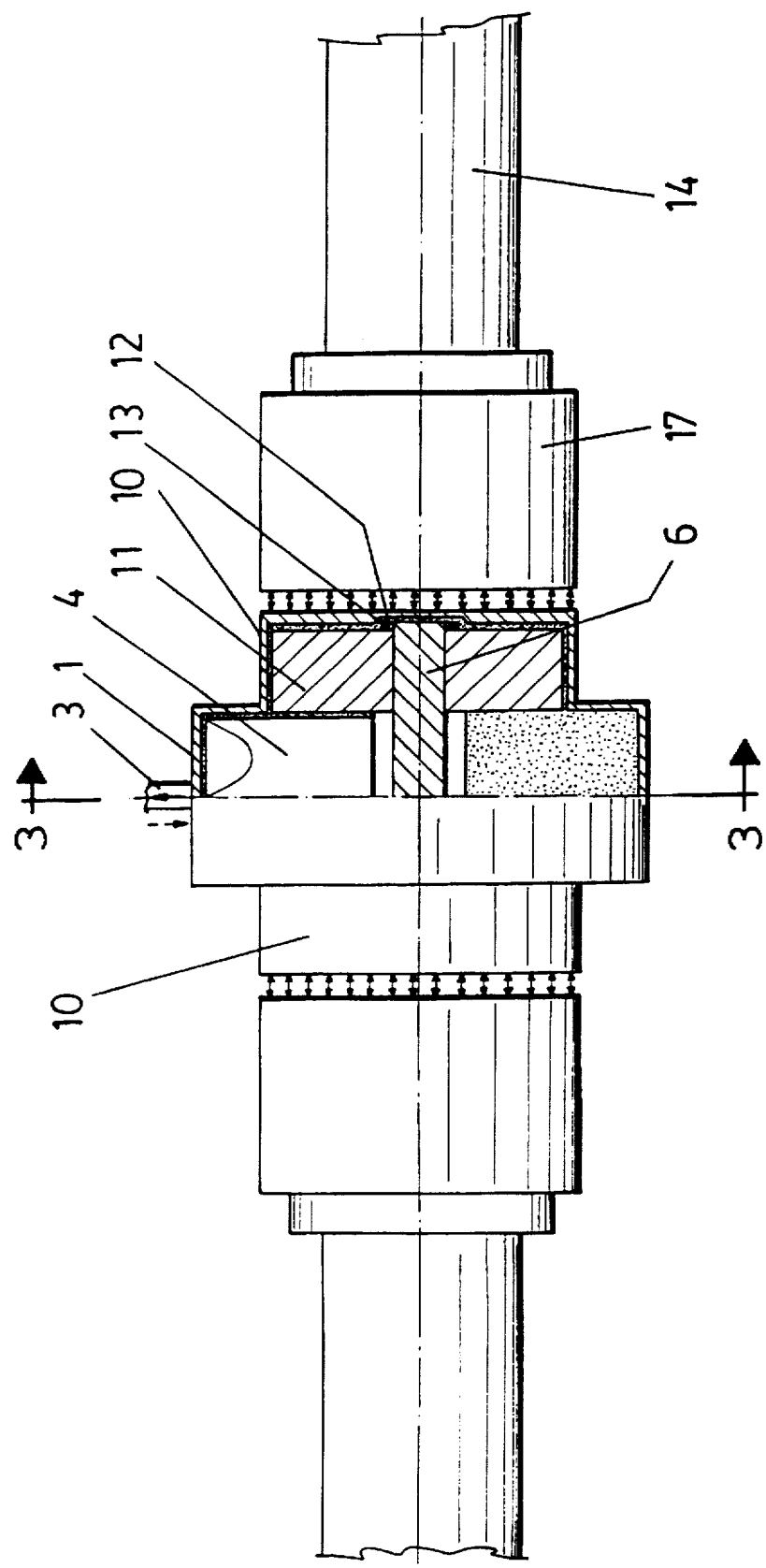
FIG. 2 is a semi-sectional, front elevational view of the pump at FIG. 1.
Figure 3:
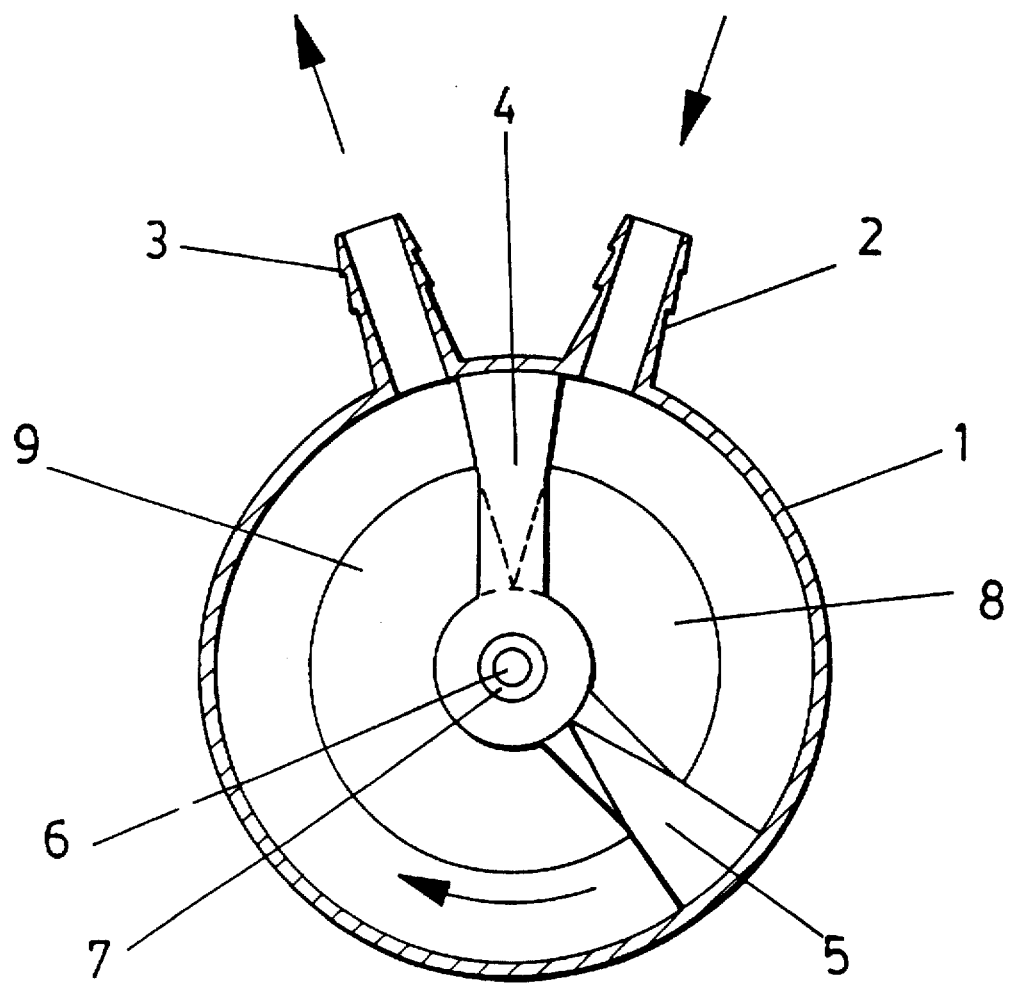
FIG. 3 is a cross-sectional, elevational view taken along line A-B of FIG. 2.

Referring to the figures, and initially to FIGS. 1 and 2, the pump system has cylindrical, body or housing (1) and has input (2) and an output (3) ports, situated radially relatively close to each other. Within the housing (1) are a pair of radial blades (4) and (5), each connected to their respective axles (6) and (7), which are coaxial, and can be situated one behind the other or concentrically mounted one on top of the other, as shown in FIG. 3. In any case the axles (6), (7) will be independently activated such that while one blade (4) is still, specifically in the space between the input (2) and output ports (3), as shown in FIG. 3, the other blade (5) is moving, performing a complete rotation of 360° until it reaches the first blade (4). At this moment the second blade (5) comes to a stop and the first blade (4) starts performing the same movement. As previously mentioned, this means that two variable volume chambers are defined, specifically an input chamber (8) and an output chamber (9) between the blades (4) and (5).

For independent and completely controlled movement of the blades (4) and (5), the housing (1) has been provided with corresponding cylindrical and hollow axial extensions (10), containing magnetic parts (11), covered with plastic and conveniently connected to their respective axles (6) and (7). To be more specific and as shown in FIG. 2, in the center of each of these hollow axial extensions (10) a small enclosure (12) is included to contain a small friction bearing (13) or similar, on which the assembly rotates, consisting in the axle (6–7) and its corresponding blade (4–5). Thus, the housing (1) is hermetically closed except for the input (2) and output (3) ports, performing the controlled movement of the blades (4) and (5).

Servomotors (14) are mounted adjacent the pump, preferably on an upper base (15) of a cabinet or bench (16). These servomotors (14) function on their respective magnetic parts (17) which, are physically independent from the magnetic parts (11), but by means of the magnetic field shown by the arrows in FIG. 2, cause the latter to be pulled and consequently, the blades (4) and (5) associated to them.

In order for the servomotors'(14) movement to adjust the pulsatile flow as close as possible to a natural flow, a Programmable Logic Controller (PLC) (18) has been provided to control the servomotors (14) through their respective power source circuits (19). The servomotors can thus be programmed from a PC (20) connected by means of a RS-232 port to the PLC (18) or through a digitalized keyboard or screen (21), type "NT20S-ST121", connected in a similar way to the PLC.

Figure 4:
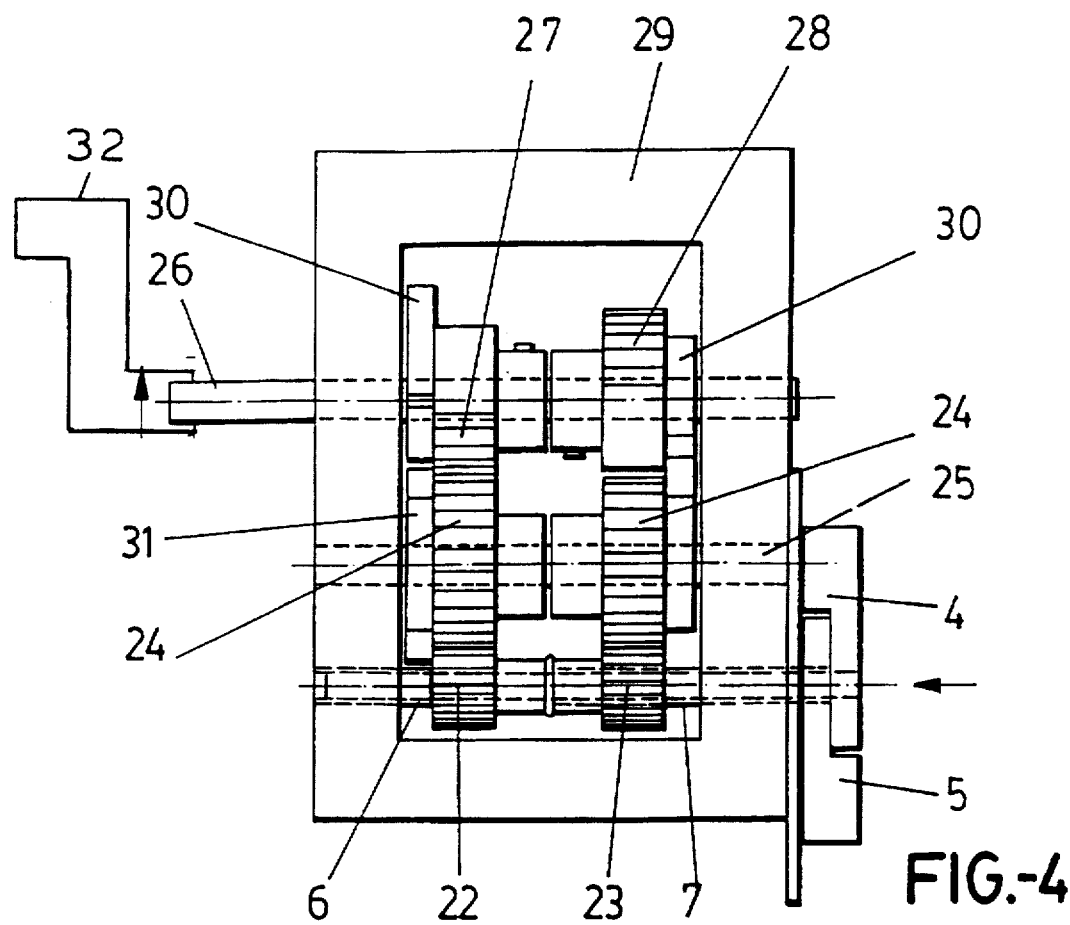
FIG. 4 is a front elevational view manual activation of auxiliary manual activation mechanism.
Figure 5:
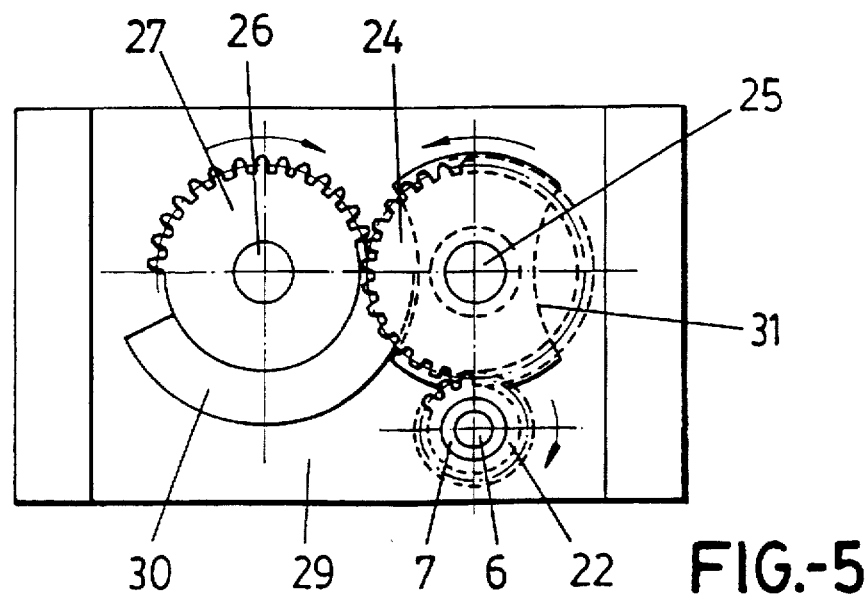
FIG. 5 is an end elevational view of the auxiliary mechanism of FIG. 4.
Figure 6:
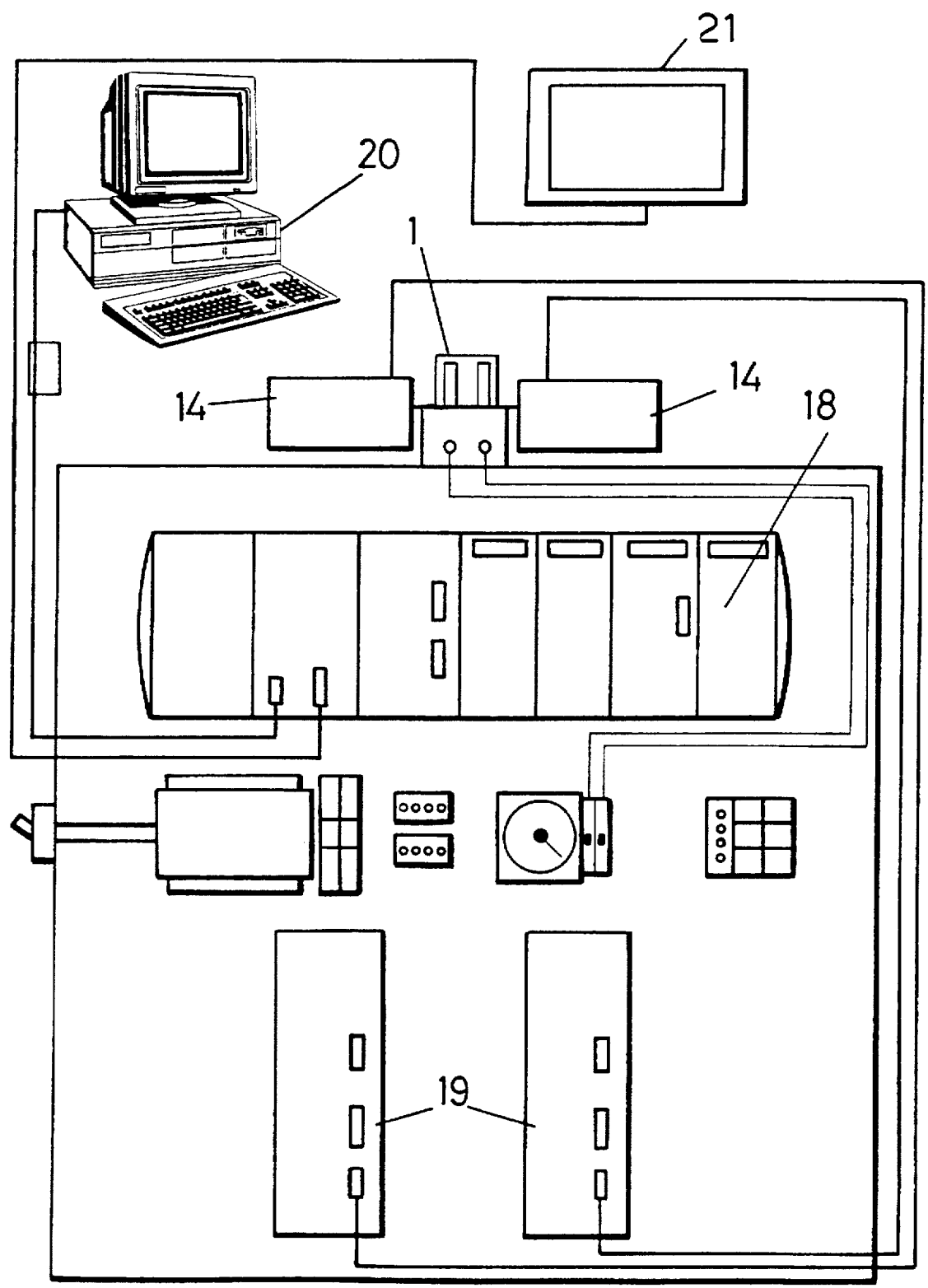
FIG. 6 is a schematic presentation of the electronic circuit which controls the pump in itself.

Finally and to complement the described structure, and since the basic security conditions of any operating room require that electrical methods can be substituted mechanically, in case of loss of electricity, it has been provided that the previously mentioned servomotors (14) collaborate with the mechanical device shown in FIGS. 4 and 5, according to which the activating axles (6) and (7) of the blades (4) and (5) are joined to their pinions (22) and (23) which, through the intermediate gears (24), mounted on an auxiliary axle (25) parallel to the previous ones, receive the movement, alternatively, from a common axle (26), which can be activated by a crank (32), through the corresponding semi-gears (27) and (28), opposite to each other, in such a way that in each complete rotation of the axle (26) during the first half of the rotation the movement is transmitted, through one of the gears (24) to the pinion (22), while in the second half of the rotation, the transmission is passed to the other pinion (23), through the other intermediate gear (24) which is freely rotatable on the corresponding axle (25). The transmission set is conveniently enclosed within a housing (29) independent from the pump's housing (1) and from which, on one side emerge the axles (6) and (7) of the blades (4) and (5), and from the other side the hand crank's axle (26).

The semi-gears (27), (28) are provided with discoidal sectors (30) which alternately align and cooperate with notches (31) of the intermediate gears (24), to immobilize the gear (24) and thus the associated blade (4) or (5) during the half rotation of the rank when the other blade is moving.

I claim:

1. An extracorporeal blood pump system, comprising:

a housing having a cavity and having two ports spaced radially along said cavity, one port being a input port and the other port being an output port, a pair of radial blades within said cavity, said blades being supported on independent axles, said blades being adapted to move independently such that one blade remains still between said input and output ports while the other is moving, thereby creating two independent chambers, an input chamber and an output chamber, independent magnetic elements connected to said axles, and two independent motor means having magnetic elements each aligned with one of said independent magnetic elements connected to said axles, thereby creating magnetic couplings therebetween, whereby said motor means can activate said two radial blades independently and without a direct connection therebetween.

2. The extracorporeal blood pump as in claim 1 wherein said housing comprises two cylindrical, axially-aligned projections, each with a friction bearing in a lateral wall thereof, said magnetic elements connected to said independent axles each being disposed within one of said projections, and said magnetic elements of said motor means being aligned outside said projections.

3. The extracorporeal blood pump system as in claim 1, wherein during operation of said pump, said blades and said magnetic elements connected to said blade supporting axles are hermetically sealed within said housing.

4. The extracorporeal blood pump system as in claim 3, wherein said pump housing and said blades are formed of plastic, and said magnetic elements connected to said axles are substantially covered in plastic.

5. The extracorporeal blood pump system as in claim 4, wherein a clearance of a predetermined small distance exists between said blades and said pump housing and between said plastic-covered magnetic elements and said pump housing whereby said clearance is to avoid producing a detrimental shearing effect on blood components.

6. The extracorporeal blood pump system as in claim 1 wherein, said pump further comprise a programmable logic controller connected to said independent motor means, said logic controller being programmable through an input device whereby preselected pump pulsation characteristics can be transmitted to said motor means.

7. The extracorporeal blood pump system as in claim 1 wherein, said axles extend outside said pump housing, and said pump system further comprises a manual activation device having a crank arm and a gearing system connected to said axles, and said manual activation device, being operable to alternately rotate one of said axles about one half rotation while holding the other axle substantially motionless.

8. The extracorporeal blood pump system as in claim 7 wherein said manual activation device further comprises, two pinion gears, each adapted to engage one of said axles, two intermediate gears, each adapted to mesh with one of said pinion gears; two semi-toothed gears mounted on a common axle, each adapted to intermittently mesh with one of said intermediate gears, said two semi-tooth gears being adapted such that while one of them transmits movement to an associated intermediate gear, the other semi-toothed gear remains inoperative, and said crank shaft being connected to said common axle.

9. The extracorporeal blood pump system as in claim 8 wherein, said two intermediate gears are independently freely rotatably mounted, said semi-gears have discoidal sectors adapted to align and cooperated with notches in said intermediate gears to immobilize an associated blade during period of non-rotation of said intermediate gears.

10. An extracorporeal blood pump system, comprising:
a housing having a cavity and having two ports spaced radially along said cavity, one port being a input port and the other port being an output port, and
a pair of radial blades within said cavity, said blades being supported on independent axles, said blades being adapted to move independently such that one blade remains still between said input and output ports while the other is moving, thereby creating two independent chambers, an input chamber and an output chamber,
said independent axles extending outside said pump housing, and said pump system further comprises a manual activation device having a crank arm and a gearing system connected to said axles, and said manual activation device, being operable to alternately rotate one of said axles about one half rotation while holding the other axle substantially motionless.

11. The extracorporeal blood pump system as in claim 10 wherein, said two intermediate gears are independently freely rotatably mounted, and said semi-gears have discoidal sectors adapted to align and cooperated with notches in said intermediate gears to immobilize an associated blade during period of non-rotation of said intermediate gears.

* * * * *